(12) United States Patent
Wan et al.

(10) Patent No.: US 7,563,803 B2
(45) Date of Patent: *Jul. 21, 2009

(54) M₃ MUSCARINIC ACETYLCHOLINE RECEPTOR ANTAGONISTS

(75) Inventors: Zehong Wan, King of Prussia, PA (US); Hongxing Yan, King of Prussia, PA (US); Michael R. Palovich, King of Prussia, PA (US); Dramane I. Laine, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 188 days.

This patent is subject to a terminal disclaimer.

(21) Appl. No.: 11/774,885

(22) Filed: Jul. 9, 2007

(65) Prior Publication Data

US 2007/0270456 A1 Nov. 22, 2007

Related U.S. Application Data

(63) Continuation of application No. 10/577,834, filed as application No. PCT/US2004/036663 on Nov. 4, 2004, now Pat. No. 7,439,255.

(60) Provisional application No. 60/517,243, filed on Nov. 4, 2003.

(51) Int. Cl.
*A61K 31/46* (2006.01)
*C07D 451/02* (2006.01)

(52) U.S. Cl. .................................. 514/304; 546/124

(58) Field of Classification Search .................. 514/304; 546/124
See application file for complete search history.

(56) References Cited

U.S. PATENT DOCUMENTS

| | | | |
|---|---|---|---|
| 2,800,478 | A | 7/1957 | Zirkle et al. |
| 2,800,481 | A | 7/1957 | Zirkle et al. |
| 3,634,852 | A | 1/1972 | Hartley et al. |
| 5,590,645 | A | 1/1997 | Davies et al. |
| 5,780,466 | A | 7/1998 | Emonds-Alt et al. |
| 5,860,419 | A | 1/1999 | Davies et al. |
| 5,873,360 | A | 2/1999 | Davies et al. |
| 6,248,752 | B1 | 6/2001 | Smith |
| 6,262,066 | B1 | 7/2001 | Tulshian et al. |
| 6,350,758 | B1 | 2/2002 | Kozikowski et al. |
| 6,455,527 | B2 | 9/2002 | Tulshian et al. |
| 6,696,462 | B2 | 2/2004 | Eickmeier et al. |
| 6,750,226 | B2 | 6/2004 | Forner et al. |
| 7,232,841 | B2 | 6/2007 | Busch-Petersen et al. |
| 7,276,521 | B2 | 10/2007 | Busch-Petersen et al. |
| 2005/0020660 | A1 | 1/2005 | Guyaux et al. |
| 2005/0113417 | A1 | 5/2005 | Mammen et al. |
| 2005/0209272 | A1 | 9/2005 | Fernandez et al. |
| 2005/0277676 | A1 | 12/2005 | Laine et al. |
| 2006/0160844 | A1 | 7/2006 | Belmonte et al. |
| 2006/0178395 | A1 | 8/2006 | Belmonte et al. |
| 2006/0178396 | A1 | 8/2006 | Belmonte et al. |
| 2007/0129396 | A1 | 6/2007 | Wan et al. |
| 2007/0135478 | A1 | 6/2007 | Palovich et al. |
| 2007/0149598 | A1 | 6/2007 | Busch-Petersen et al. |
| 2007/0173646 | A1 | 7/2007 | Laine et al. |
| 2007/0179180 | A1 | 8/2007 | Busch-Petersen et al. |
| 2007/0179184 | A1 | 8/2007 | Busch-Petersen et al. |
| 2007/0185088 | A1 | 8/2007 | Busch-Petersen et al. |
| 2007/0185090 | A1 | 8/2007 | Busch-Petersen et al. |
| 2007/0185148 | A1 | 8/2007 | Busch-Petersen et al. |
| 2007/0185155 | A1 | 8/2007 | Laine et al. |
| 2007/0232599 | A1 | 10/2007 | Palovich et al. |

FOREIGN PATENT DOCUMENTS

| | | |
|---|---|---|
| EP | 0069715 | 6/1982 |
| GB | 2064336 | 6/1981 |
| GB | 2129691 | 5/1984 |
| GB | 2169265 | 7/1986 |
| GB | 2178965 | 2/1987 |
| GB | 2242134 | 9/1991 |
| WO | 87/05213 | 9/1987 |
| WO | 2004/012684 | 2/2004 |
| WO | 2006/050239 | 5/2006 |
| WO | 2006/055503 | 5/2006 |
| WO | 2006/055553 | 5/2006 |
| WO | 2006/062883 | 6/2006 |
| WO | 2006/062931 | 6/2006 |
| WO | 2006/065788 | 6/2006 |
| WO | 2006065755 | 6/2006 |
| WO | 2007/016639 | 2/2007 |
| WO | 2007/016650 | 2/2007 |
| WO | 2007/018508 | 2/2007 |
| WO | 2007/018514 | 2/2007 |
| WO | 2007/022351 | 2/2007 |

OTHER PUBLICATIONS

Brown, *History and Basic Properties*, Humana Press, USA pp. 7-9 (1989).
Caulfield, *Pharmac Ther.*, vol. 58 pp. 319-379 (1993).
Costello, et al., *American Journal of Physiology*, vol. 276 (5) pp. L709-L714 (1999).
Fryer and Jacoby, *Am J Respir Crit Care Med*, vol. 158 (5, pt 3) pp. 154-160 (1998).
Fryer et al., *Life Sci*, vol. 64 (6-7) pp. 449-455 (1999).
Hedge, et al., *Life Sciences*, vol. 64 (6/7) pp. 419-428 (1999).
Ikeda, et al., *Naunyn-Schmiedeberg's Arch Pharmacol.*, vol. 366, pp. 97-103, (2002).
Minette, et al., *Journal of Applied Physiology*, vol. 67(6) pp. 2461-2465 (1989).
Oprins, et al., *Annals of the New York Academy of Sciences*, vol. 915 pp. 102-106 (2000).
Pauwels et al., *Am. J. Respir. Crit. Care Med.*, vol. 163 pp. 1256-1276 (2001).

(Continued)

*Primary Examiner*—Charanjit S Aulakh
(74) *Attorney, Agent, or Firm*—Dara L. Dinner; Charlas M. Kinzig

(57) ABSTRACT

Muscarinic Acetylcholine receptor antagonists and methods of using them are provided.

23 Claims, No Drawings

OTHER PUBLICATIONS

Ran, et al., *Yaoxue Xuebao*, vol. 19 (5) pp. 361-366 (1984) Abstract only.
Sarau, *Mol. Pharmacol.*, vol. 56 (3) p. 657-63 (1999).
Van Rossum, et al., *Arch. Int. Pharmacodyn.*, vol. 143 p. 299 (1963) Best Available Copy.
Wu, et al., *Zhongguo Yaowu Huazue Zazhi*, vol. 3 (1) pp. 23-26 (1993) Abstract only.
Zirkle, et al., *J. Med Chem*, vol. 27 pp. 1269-1279 (1962).
Zirkle, et al., *J. Med Chem*, vol. 27 pp. 1279-1285 (1962).
Zirkle, et al., *J Med Chem*, vol. 5 pp. 341-356 (1962).
Zhang, et al., *J Med Chem*, vol. 44 pp. 3937-3945 (2001).
Laine, et al. U.S. Appl. No. 10/585,830, filed Jul. 12, 2006.
Budzik, et al. U.S. Appl. No. 10/598,743, filed Sep. 11, 2009.
Jin, et al. U.S. Appl. No. 10/598,750, filed Sep. 11, 2009.
Laine, et al. U.S. Appl. No. 10/599,717, filed Oct. 6, 2006.
Cooper, et al. U.S. Appl. No. 11/570,981, filed Dec. 20, 2006.
Busch-Petersen, et al. U.S. Appl. No. 11/573,097, filed Feb. 2, 2007.
Busch-Petersen, et al. U.S. Appl. No. 11/573,099, filed Feb. 2, 2007.
Busch-Petersen, et al. U.S. Appl. No. 11/766,318, filed Jun. 21, 2007.
Busch-Petersen, et al. U.S. Appl. No. 11/766,371, filed Jun. 21, 2007.
Laine, et al. U.S. Appl. No. 11/774,867, filed May 3, 2007.
Ran, et al., *Yaoxue Xuebao*, vol. 19 (5) pp. 361-366 (1984), with translation.
Wu, et al., *Zhongguo Yaowu Huaxue Zazhi*, vol. 3(1) pp. 23-26 (1993), with translation.
Yu, et al., *Yaoxue Xuebao*, vol. 18(10) pp. 766-774 (1983), with translation.
Zhang, et al., *Yaoxue Xuebao*, vol. 20(10) pp. 752-758 (1985), with translation.

$M_3$ MUSCARINIC ACETYLCHOLINE RECEPTOR ANTAGONISTS

This application is a continuation application of U.S. Ser. No. 10/577,834, filed 1 May 2006 now U.S. Pat. No. 7,439,255, which is the §371 national stage entry of PCT/US2004/036663, filed 4 Nov. 2004 and which claims the benefit of priority from U.S. Ser. No. 60/517,243, filed 4 Nov. 2003.

FIELD OF THE INVENTION

This invention relates to novel derivatives of 8-azoniabicyclo[3,2,1]octanes, pharmaceutical compositions, processes for their preparation, and use thereof in treating $M_3$ muscarinic acetylcholine receptor mediated diseases.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs where they mediate many of the vital functions. Muscarinic receptors can mediate both inhibitory and excitatory actions. For example, in smooth muscle found in the airways, $M_3$ mAChRs mediate contractile responses. For review, please see Caulfield (1993 *Pharmac. Ther.* 58:319-79).

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 *Am J Respir Crit Care Med* 158(5, pt 3) S 154-60).

Three subtypes of mAChRs have been identified as important in the lungs, $M_1$, $M_2$ and $M_3$ mAChRs. The $M_3$ mAChRs, located on airway smooth muscle, mediate muscle contraction. Stimulation of $M_3$ mAChRs activates the enzyme phospholipase C via binding of the stimulatory G protein Gq/11 (Gs), leading to liberation of phosphatidyl inositol-4,5-bisphosphate, resulting in phosphorylation of contractile proteins. $M_3$ mAChRs are also found on pulmonary submucosal glands. Stimulation of this population of $M_3$ mAChRs results in mucus secretion.

$M_2$ mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal $M_2$ mAChRs are located on postganglionic parasympathetic nerves. Under normal physiologic conditions, neuronal $M_2$ mAChRs provide tight control of acetylcholine release from parasympathetic nerves. Inhibitory $M_2$ mAChRs have also been demonstrated on sympathetic nerves in the lungs of some species. These receptors inhibit release of noradrenaline, thus decreasing sympathetic input to the lungs.

$M_1$ mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation (Fryer et al. 1999 *Life Sci* 64 (6-7) 449-55). This mAChR dysfunction results in airway hyperreactivity and hyperresponsiveness mediated by increased stimulation of $M_3$ mAChRs. Thus the identification of potent mAChR antagonists would be useful as therapeutics in these mAChR-mediated disease states.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 *Am. J. Respir. Crit. Care Med.* 163:1256-1276).

Despite the large body of evidence supporting the use of anti-cholinergic therapy for the treatment of airway hyperreactive diseases, relatively few anti-cholinergic compounds are available for use in the clinic for pulmonary indications. More specifically, in United States, Ipratropium Bromide (Atrovent©; and Combivent©, in combination with albuterol) is currently the only inhaled anti-cholinergic marketed for the treatment of airway hyperreactive diseases. While this compound is a potent anti-muscarinic agent, it is short acting, and thus must be administered as many as four times daily in order to provide relief for the COPD patient. In Europe and Asia, the long-acting anti-cholinergic Tiotropium Bromide (Spiriva©) was recently approved, however this product is currently not available in the United States. Thus, there remains a need for novel compounds that are capable of causing blockade at mAChRs which are long acting and can be administered once-daily for the treatment of airway hyperreactive diseases such as asthma and COPD.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anticholinergic use.

SUMMARY OF THE INVENTION

This invention provides for a method of treating a muscarinic acetylcholine receptor (mAChR) mediated disease, wherein acetylcholine binds to an $M_3$ mAChR and which method comprises administering an effective amount of a compound of Formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

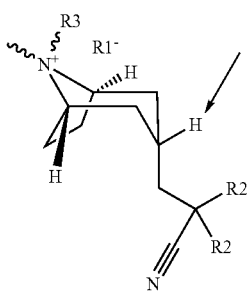

(I)

DETAILED DESCRIPTION OF THE INVENTION

This invention relates to novel derivatives of 8-azoniabicyclo[3,2,1]octanes, pharmaceutical compositions, processes for their preparation, and use thereof in treating $M_3$ muscarinic acetylcholine receptor mediated diseases, represented by Formula (I)

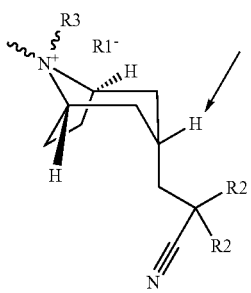

(I)

wherein:

the H atom indicated is in the exo position;

R1⁻ represents an anion associated with the positive charge of the N atom.

R1⁻ may be but is not limited to chloride, bromide, iodide, sulfate, benzene sulfonate and toluene sulfonate;

R2 is selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;

R3 is selected from the group consisting of $(C_2-C_{12})$alkyl, $(C_1-C_6)$alkenyl, $(C_1-C_6)$alkyl$(C_3-C_6)$cycloalkyl, $(C_1-C_6)$alkyl-phenyl, $(C_1-C_6)$alkyl-OH, $(C_1-C_6)$alkyl-CN, $(C_1-C_6)$alkyl-halogen, $(C_1-C_6)$alkyl-CF$_3$, $(C_1-C_6)$alkyl-OCH$_3$, $(C_1-C_6)$alkyl-O—$(C_1-C_6)$alkyl-OCH$_3$ and $(C_1-C_6)$alkyl-O—$(C_1-C_6)$aryl. Preferred R3 substituents are in the endo position.

All of the aryl, heteroaryl, and heterocyclic containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)_{m'}$ $C_{1-10}$ alkyl, wherein m' is 0, 1 or 2, such as methyl thio, methyl sulfinyl or methyl sulfonyl; amino, mono & di-substituted amino, such as in the $NR_4R_5$ group; $NHC(O)R_4$; $C(O)NR_4R_5$; $C(O)OH$; $S(O)_2NR_4R_5$; $NHS(O)_2R_4$, $C_{1-10}$ alkyl, such as methyl, ethyl, propyl, isopropyl, or t-butyl; halosubstituted $C_{1-10}$ alkyl, such as $CF_3$; an optionally substituted aryl, such as phenyl, or an optionally substituted arylalkyl, such as benzyl or phenethyl, optionally substituted heterocylic, optionally substituted heterocyclicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl; $C_{1-10}$ alkoxy; $S(O)_{m'}C_{1-10}$ alkyl; amino, mono & di-substituted alkyl amino, such as in the $NR_4R_5$ group; $C_{1-10}$ alkyl, or halosubstituted $C_{1-10}$ alkyl, such as $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited to, pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl" or "heterocycloalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S(O) of the corresponding sulfide, the term "thio" refers to the sulfide, and the term "sulfonyl" refers to the fully oxidized $S(O)_2$ moiety.

Preferred compounds useful in the present invention include:

(3-Endo)-3-(2-cyano-2,2-diphenylethyl)-8-(cyclohexyl methyl)-8-methyl-8-azoniabicyclo[3.2.1]octane bromide;
(3-Endo)-3-(2-cyano-2,2-diphenylethyl)-8-(cyclopropyl methyl)-8-methyl-8-azoniabicyclo[3.2.1]octane bromide;
(3-Endo)-8-butyl-3-(2-cyano-2,2-diphenylethyl)-8-methyl-8-azoniabicyclo[3.2.1]octane bromide;
(3-Endo)-8-(4-chlorobutyl)-3-(2-cyano-2,2-diphenylethyl)-8-methyl-8-azoniabicyclo[3.2.1]octane bromide;
(3-Endo)-3-(2-cyano-2,2-diphenylethyl)-8-dodecyl-8-methyl-8-azoniabicyclo[3.2.1]octane bromide;
(3-Endo)-3-(2-cyano-2,2-diphenylethyl)-8-methyl-8-(2-propen-1-yl)-8-azoniabicyclo[3.2.1]octane iodide;
(3-Endo)-3-(2-cyano-2,2-diphenylethyl)-8-methyl-8-(phenylmethyl)-8-azoniabicyclo[3.2.1]octane bromide;
(3-Endo)-3-(2-cyano-2,2-diphenylethyl)-8-(2-hydroxyethyl)-8-methyl-8-azoniabicyclo[3.2.1]octane bromide;
(3-Endo)-3-(2-cyano-2,2-diphenylethyl)-8-ethyl-8-methyl-8-azoniabicyclo[3.2.1]octane bromide;
(3-Endo)-3-(2-cyano-2,2-diphenylethyl)-8-methyl-8-propyl-8-azoniabicyclo[3.2.1]octane bromide;
(3-Endo)-3-(2-cyano-2,2-diphenylethyl)-8-(5-hexen-1-yl)-8-methyl-8-azoniabicyclo[3.2.1]octane bromide;
(3-Endo)-3-(2-cyano-2,2-diphenylethyl)-8-methyl-8-(4,4,4-trifluorobutyl)-8-azoniabicyclo[3.2.1]octane bromide;
(3-Endo)-3-(2-cyano-2,2-diphenylethyl)-8-methyl-8-(3-phenyl propyl)-8-azoniabicyclo[3.2.1]octane bromide;
(3-Endo)-3-(2-cyano-2,2-diphenylethyl)-8-(2-cyclohexylethyl)-8-methyl-8-azoniabicyclo[3.2.1]octane bromide;
(3-Endo)-3-(2-cyano-2,2-diphenylethyl)-8-(3-cyanopropyl)-8-methyl-8-azoniabicyclo[3.2.1]octane bromide;
(3-Endo)-3-(2-cyano-2,2-diphenylethyl)-8-methyl-8-[2-(methyloxy)ethyl]-8-azoniabicyclo[3.2.1]octane bromide;
(3-Endo)-3-(2-cyano-2,2-diphenylethyl)-8-methyl-8-(2-{[2-(methyloxy)ethyl]oxy}ethyl)-8-azoniabicyclo[3.2.1]octane bromide;
N-(Endo)-(3-endo)-3-(2-cyano-2,2-diphenylethyl)-(8-endo)-8-(5-hexen-1-yl)-8-methyl-8-azoniabicyclo[3.2.1]octane bromide;
N-(Endo)-(3-endo)-(2-cyano-2,2-diphenylethyl)-(8-endo)-methyl-8-{2-[(phenylmethyl)oxy]ethyl}-8-azoniabicyclo[3.2.1]octane bromide;
N-(Endo)-(3-endo)-(2-cyano-2,2-diphenylethyl)-8-methyl-8-(3-phenylpropyl)-8-azoniabicyclo[3.2.1]octane bromide; and
N-(Endo)-(3-endo)-(2-cyano-2,2-diphenylethyl)-8-methyl-8-[3-(phenyloxy)propyl]-8-azoniabicyclo[3.2.1]octane bromide.

Methods of Preparation

Preparation

The compounds of Formula (I) may be obtained by applying synthetic procedures, some of which are illustrated in the Schemes below. The synthesis provided for these Schemes is applicable for producing compounds of Formula (I) having a variety of different R1, R2 and R3 which are reacted, employing substituents which are suitable protected, to achieve compatibility with the reactions outlined herein. Subsequent deprotection, in those cases, then affords compounds of the nature generally disclosed. While some Schemes are shown with specific compounds, this is merely for illustration purpose only.

A general preparation method is shown in Scheme I. The synthesis started with compound 1. Coupling reaction with the anion derived from HC(CN)(R2)(R2) provided 2. Treatment with R3-R1 then furnished the quaternary ammonium salt with Formula (I).

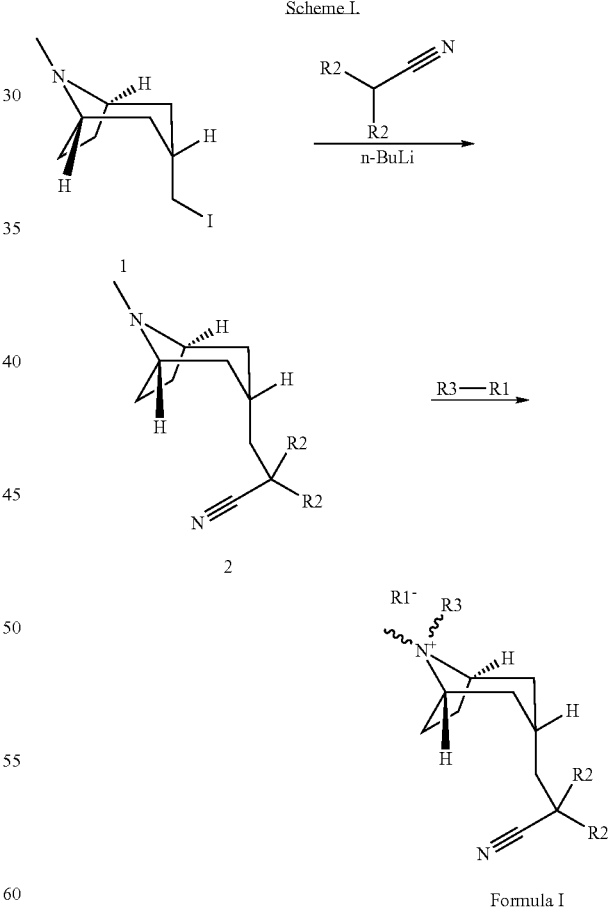

Scheme I.

A more specific preparation method leading to compounds with Formula (I) is outlined in Scheme II. Alkylation of diphenylacetonitrile with 1 afforded compound 3. Treatment with $CF_3(CH_2)_3Br$ then afforded quarternary ammonium salt 4.

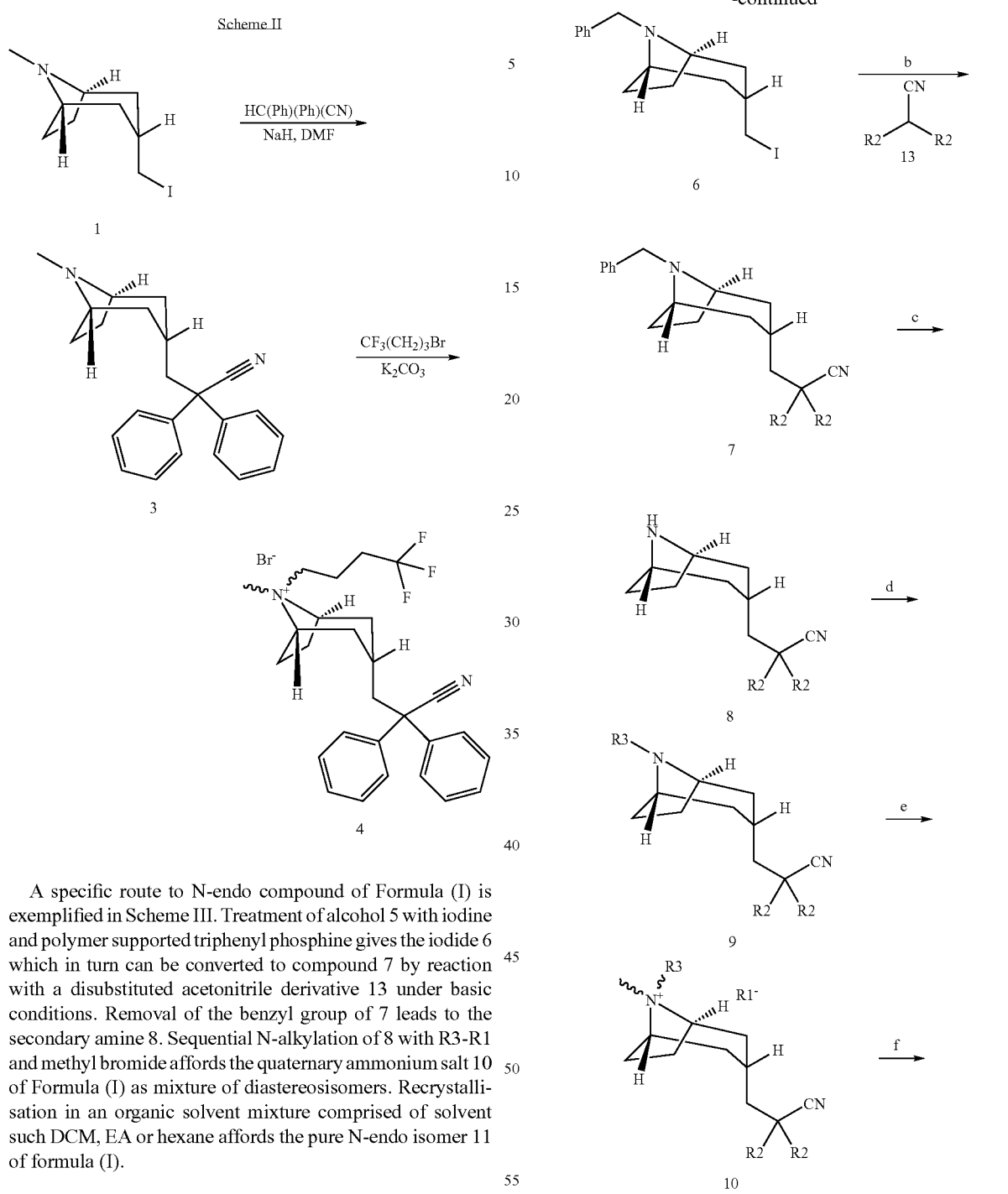

A specific route to N-endo compound of Formula (I) is exemplified in Scheme III. Treatment of alcohol 5 with iodine and polymer supported triphenyl phosphine gives the iodide 6 which in turn can be converted to compound 7 by reaction with a disubstituted acetonitrile derivative 13 under basic conditions. Removal of the benzyl group of 7 leads to the secondary amine 8. Sequential N-alkylation of 8 with R3-R1 and methyl bromide affords the quaternary ammonium salt 10 of Formula (I) as mixture of diastereoisomers. Recrystallisation in an organic solvent mixture comprised of solvent such DCM, EA or hexane affords the pure N-endo isomer 11 of formula (I).

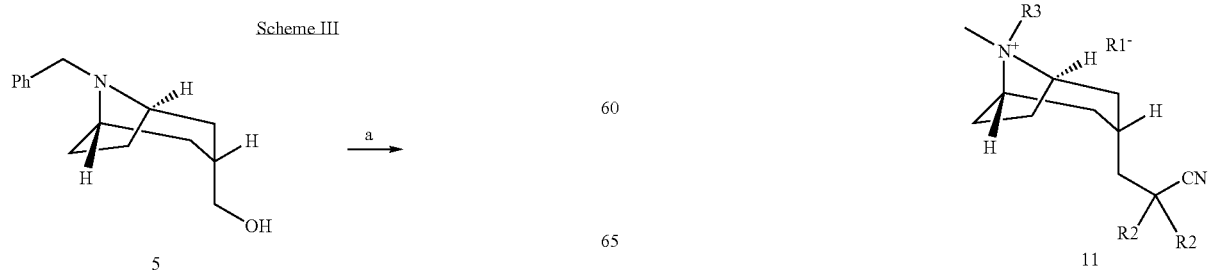

-continued

Reagents and conditions:
a Iodine, Polymer supported triphenyl phosphine, DCM;
b NaH, DMF;
c ClCO₂CHClCH₃, mw, 140° C. or H₂, 10% Pd(OH)₂;
d R3-R1, K₂CO₃, acetonitrile;
e MeBr, acetone;
f recrystallisation.

Alternatively the secondary amine 8 can de prepared from the N-Boc protected alcohol derivative 14 by generation of a tosylate derivative which can be displaced by the disubstituted acetonitrile 13 with concomitant removal of the BOC group as depicted in Scheme IV.

Scheme IV

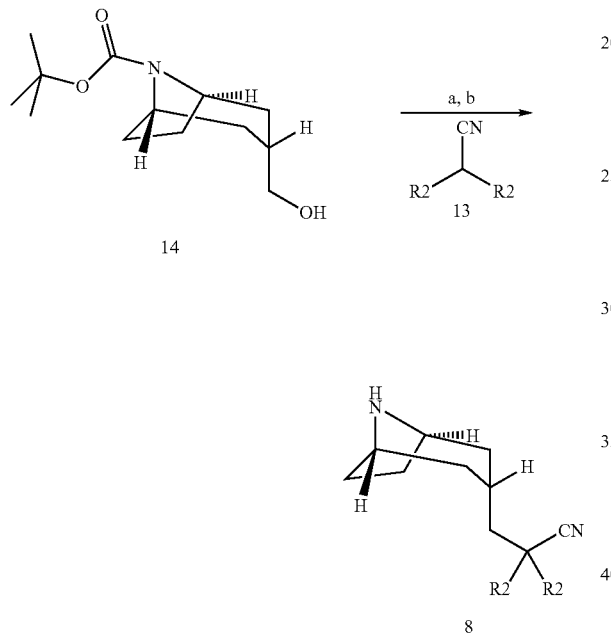

Reagents and conditions:
a Tosyl chlorode, TEA;
b NaH, DMF

SYNTHETIC EXAMPLES

The invention will now be described by reference to the following Examples which are merely illustrative and are not to be construed as a limitation of the scope of the present invention. Most reagents and intermediates are commercially available or are prepared according to procedures in the literature. The preparation of intermediates not described in the literature is also illustrated below.

Flash column chromatography was carried out using Merck 9385 silica unless stated otherwise.

LC/MS analyses were conducted under the following conditions:

Column: 3.3 cm×4.6 mm ID, 3 um ABZ+PLUS

Flow Rate: 3 ml/min

Injection Volume: 5 μl

Temp: Room temperature

Solvents: A: 0.1% Formic Acid+10 mMolar Ammonium Acetate.
B: 95% Acetonitrile+0.05% Formic Acid

|  | Time | A % | B % |
|---|---|---|---|
| Gradient: | 0.00 | 100 | 0 |
|  | 0.70 | 100 | 0 |
|  | 4.20 | 0 | 100 |
|  | 5.30 | 0 | 100 |
|  | 5.50 | 100 | 0 |

The Gilson preparatory HPLC was conducted under the following conditions:

Column: 75×33 mm I.D., S-5 um, 12 nm

Flow rate: 30 mL/min

Injection Volume: 0.800 mL

Room temperature

Solvent A: 0.1% trifluoroacetic acid in water

Solvent B: 0.1% trifluoroacetic acid in acetonitrile

Intermediate 1

Preparation of 3-((endo)-8-methyl-8-aza-bicyclo [3.2.1]oct-3-yl)-2,2-diphenyl-propionitrile

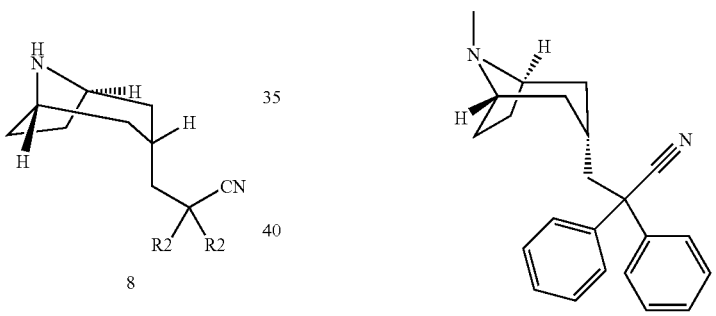

a) Preparation of ((endo)-8-methyl-8-aza-bicyclo[3.2.1]oct-3-yl)-methanol

A mixture of 1,1-dimethylethyl(endo)-3-(hydroxymethyl)-8-azabicyclo[3.2.1]octane-8-carboxylate (0.50 g, 2.05 mmol) and LiAlH₄ (6.16 mL, 1.0 M in THF, 6.16 mmol) was heated at 80° C. in a microwave reactor for 60 min. The solution was then mixed with saturated Na₂SO₄ solution, filtered through celite and concentrated to afford the title compound (0.31 g, 97%): LCMS (ES) m/z 156 (M+H)⁺; ¹H-NMR (CDCl₃) δ 1.28 (s, 1H), 1.59 (m, 4H), 1.90 (m, 1H), 2.13 (m, 4H), 2.32 (s, 3H), 3.17 (s, 2H), 3.59 (d, 2H).

b) Preparation of (endo)-3-iodomethyl-8-methyl-8-aza-bicyclo[3.2.1]octane

A solution of iodine (6.67 g, 25.8 mmol) and ((endo)-8-methyl-8-aza-bicyclo[3.2.1]oct-3-yl)-methanol (2.0 g, 12.9 mmol) in CH₂Cl₂ (120 mL) was mixed with PPh₃ (on resin, 8.6 g, 3 mmol/g, 25.8 mmol). The resultant mixture was stirred for 17 hours, filtered and concentrated to afford title compound (2.63 g, 77%): LCMS (ES) m/z 266 (M+H)⁺; ¹H-NMR (CDCl₃) δ 2.05 (m, 4H), 2.39 (m, 3H), 2.79 (d, 3H), 2.98 (m, 2H), 3.45 (d, 2H), 3.81 (s, 2H).

c) Preparation of 3-((endo)-8-methyl-8-aza-bicyclo[3.2.1]oct-3-yl)-2,2-diphenyl-propionitrile A solution of (endo)-3-iodomethyl-8-methyl-8-azabicyclo[3.2.1]octane (1.06 g, 4.0 mmol) and Ph$_2$CHCN (2.32 g, 12.0 mmol) in DMF (20 mL) was mixed with NaH (0.288 g, 12.0 mmol). The resultant mixture was stirred at room temperature for 60 minutes. Filtration and purification via a reverse phase HPLC (Gilson) then afforded the title compound (1.16 g, 93%): LCMS (ES) m/z 331 (M+H)$^+$; $^1$H-NMR (CDCl$_3$) δ 1.64 (m, 2H), 2.14 (m, 1H), 2.26 (m, 2H), 2.34 (m, 2H), 2.52 (m, 2H), 2.75 (m, 5H), 3.83 (s, 2H), 7.39 (d, 10H).

General Preparation Procedures

A solution of 3-((3-endo)-8-methyl-8-aza-bicyclo[3.2.1]oct-3-yl)-2,2-diphenyl-propionitrile (33.0 mg, 0.10 mmol) in CH$_2$Cl$_2$ (0.5 mL) and MeCN (0.5 mL) was mixed with RBr (1.0 mmol) and K$_2$CO$_3$ (27.6 mg, 0.20 mmol). The resultant mixture was stirred at room temperature for certain reaction time (specified in following examples). It was then diluted with DMSO (0.3 mL) and concentrated. Purification via a reverse phase HPLC (Gilson) afforded the target compound.

Example 1

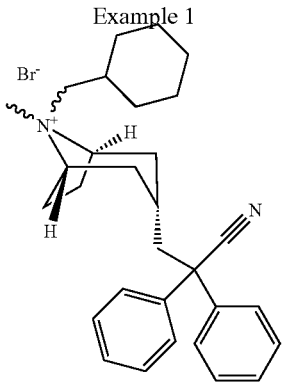

(3-endo)-3-(2-cyano-2,2-diphenylethyl)-8-(cyclohexylmethyl)-8-methyl-8-azoniabicyclo[3.2.1]octane bromide The title compound was prepared in 15% yield by following the general experimental procedure (reaction time=7 days): LCMS (ES) m/z 427 (M)$^+$; $^1$H-NMR (CDCl$_3$) δ 1.29 (m, 3H), 1.43 (m, 2H), 1.83 (m, 8H), 2.19 (m, 1H), 2.42 (m, 6H), 3.00 (m, 2H), 3.04 (s, 3H), 3.10 (d, 2H), 3.84 (s, 2H), 7.35 (m, 2H), 7.43 (m, 4H), 7.49 (m, 4H).

Example 2

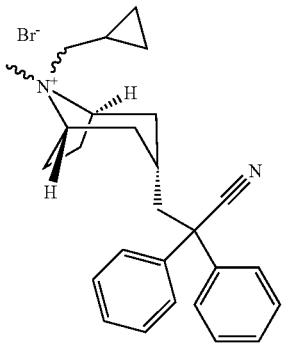

(3-endo)-3-(2-cyano-2,2-diphenylethyl)-8-(cyclopropylmethyl)-8-methyl-8-azoniabicyclo[3.2.1]octane bromide The title compound was prepared in 51% yield by following the general experimental procedure (reaction time=70 hours): LCMS (ES) m/z 385 (M)$^+$; $^1$H-NMR (CDCl$_3$) δ 0.48 (m, 2H), 0.83 (m, 2H), 1.13 (m, 1H), 1.82 (m, 2H), 2.22 (m, 1H), 2.42 (m, 6H), 3.01 (m, 2H), 3.12 (m, 3H), 3.19 (d, 2H), 3.90 (m, 2H), 7.35 (m, 2H), 7.43 (m, 4H), 7.50 (m, 4H).

Example 3

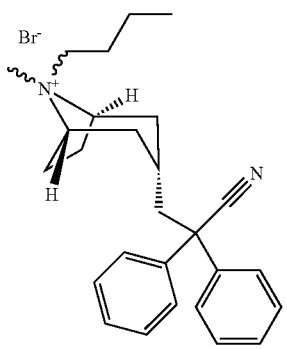

(3-endo)-8-butyl-3-(2-cyano-2,2-diphenylethyl)-8-methyl-8-azoniabicyclo[3.2.1]octane bromide The title compound was prepared in 26% yield by following the general experimental procedure (reaction time=70 hours): LCMS (ES) m/z 387 (M)$^+$; $^1$H-NMR (CDCl$_3$) δ 1.04 (m, 3H), 1.45 (m, 2H), 1.74 (m, 2H), 1.84 (d, 2H), 2.21 (m, 1H), 2.45 (m, 6H), 3.00 (m, 2H), 3.02 (s, 3H), 3.20 (m, 2H), 3.83 (s, 2H), 7.35 (m, 2H), 7.42 (m, 4H), 7.49 (m, 4H).

Example 4

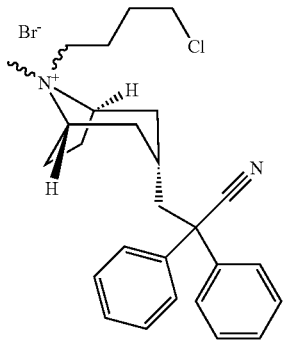

(3-endo)-8-(4-chlorobutyl)-3-(2-cyano-2,2-diphenylethyl)-8-methyl-8-azoniabicyclo[3.2.1]octane bromide The title compound was prepared in 37% yield by following the general experimental procedure (reaction time=70 hours): LCMS (ES) m/z 421 (M)$^+$; $^1$H-NMR (CDCl$_3$) δ 1.88

(m, 6H), 2.18 (m, 1H), 2.45 (m, 6H), 3.01 (m, 2H), 3.04 (s, 3H), 3.28 (m, 2H), 3.67 (m, 2H), 3.84 (s, 2H), 7.35 (m, 2H), 7.42 (m, 4H), 7.49 (m, 4H).

Example 5

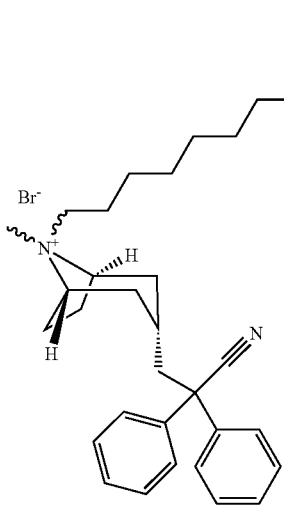

(3-endo)-3-(2-cyano-2,2-diphenylethyl)-8-dodecyl-8-methyl-8-azoniabicyclo[3.2.1]octane bromide The title compound was prepared in 10% yield by following the general experimental procedure (reaction time=70 hours): LCMS (ES) m/z 499 (M)$^+$; $^1$H-NMR (CDCl$_3$) δ 0.95 (t, 3H), 1.36 (m, 18H), 1.73 (m, 2H), 1.82 (d, 2H), 2.18 (m, 1H), 2.46 (m, 6H), 3.00 (d, 2H), 3.02 (s, 3H), 3.19 (m, 2H), 3.82 (s, 2H), 7.35 (m, 2H), 7.42 (m, 4H), 7.49 (m, 4H).

Example 6

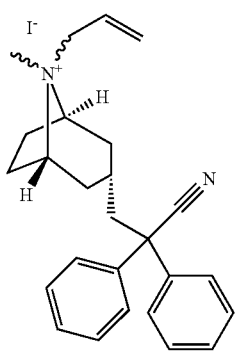

(3-endo)-3-(2-cyano-2,2-diphenylethyl)-8-methyl-8-(2-Propen-1-yl)-8-azoniabicyclo[3.2.1]octane iodide The title compound was prepared in 37% yield by following the general experimental procedure (reaction time=3 hours): LCMS (ES) m/z 371 (M)$^+$; $^1$H-NMR (CDCl$_3$) δ 1.83 (m, 2H), 2.20 (m, 1H), 2.36 (m, 2H), 2.47 (m, 4H), 3.02 (m, 5H), 3.85 (s, 2H), 3.92 (d, 2H), 5.71 (m, 2H), 6.09 (m, 1H), 7.35 (m, 2H), 7.42 (m, 4H), 7.51 (m, 4H).

Example 7

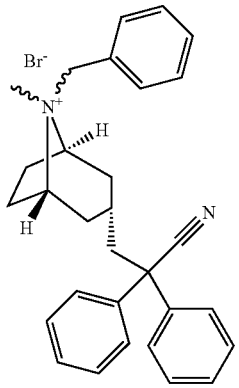

(3-endo)-3-(2-cyano-2,2-diphenylethyl)-8-methyl-8-(phenylmethyl)-8-azoniabicyclo[3.2.1]octane bromide The title compound was prepared in 39% yield by following the general experimental procedure (reaction time=3 hours): LCMS (ES) m/z 421 (M)$^+$; $^1$H-NMR (CDCl$_3$) δ 1.85 (d, 2H), 2.17 (m, 1H), 2.45 (m, 4H), 2.73 (m, 2H), 2.92 (s, 3H), 3.04 (d, 2H), 3.86 (s, 2H), 4.45 (s, 2H), 7.34 (m, 2H), 7.42 (m, 4H), 7.48 (m, 4H), 7.56 (m, 5H).

Example 8

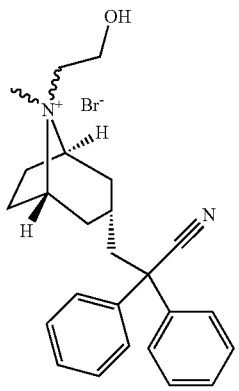

(3-endo)-3-(2-cyano-2,2-diphenylethyl)-8-(2-hydroxyethyl)-8-methyl-8-azoniabicyclo[3.2.1]octane bromide The title compound was prepared in 40% yield by following the general experimental procedure (reaction time=10 days): LCMS (ES) m/z 375 (M)$^+$; $^1$H-NMR (CDCl$_3$) δ 1.84

(m, 2H), 2.04 (m, 1H), 2.22 (m, 2H), 2.34 (m, 2H), 2.50 (m, 2H), 2.74 (s, 1H), 2.95 (d, 1H), 3.01 (d, 1H), 3.14 (s, 1H), 3.33 (s, 3H), 3.40 (m, 1H), 3.81 (m, 1H), 3.99 (m, 2H), 7.35 (m, 2H), 7.42 (m, 4H), 7.48 (m, 4H).

Example 9

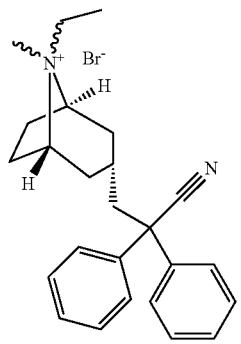

(3-endo)-3-(2-cyano-2,2-diphenylethyl)-8-ethyl-8-methyl-8-azoniabicyclo[3.2.1]octane bromide The title compound was prepared in 60% yield by following the general experimental procedure (reaction time=70 hours): LCMS (ES) m/z 359 (M)$^+$; $^1$H-NMR (CDCl$_3$) δ 1.32 (t, 3H), 1.83 (d, 2H), 2.21 (m, 1H), 2.36 (m, 4H), 2.52 (m, 2H), 3.02 (m, 5H), 3.35 (m, 2H), 3.81 (s, 2H), 7.35 (m, 2H), 7.42 (m, 4H), 7.49 (m, 4H).

Example 10

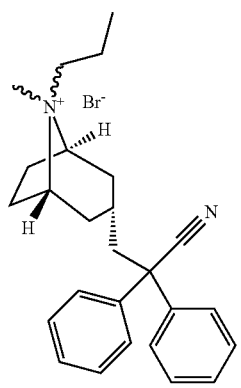

(3-endo)-3-(2-cyano-2,2-diphenylethyl)-8-methyl-8-propyl-8-azoniabicyclo[3.2.1]octane bromide The title compound was prepared in 20% yield by following the general experimental procedure (reaction time=70 hours): LCMS (ES) m/z 373 (M)$^+$; $^1$H-NMR (CDCl$_3$) δ 1.02 (t, 3H), 1.74 (m, 1H), 1.81 (d, 2H), 2.18 (m, 1H), 2.34 (m, 2H), 2.45 (m, 4H), 3.00 (m, 2H), 3.02 (s, 3H), 3.17 (m, 2H), 3.82 (s, 2H), 7.35 (m, 2H), 7.42 (m, 4H), 7.49 (m, 4H).

Example 11

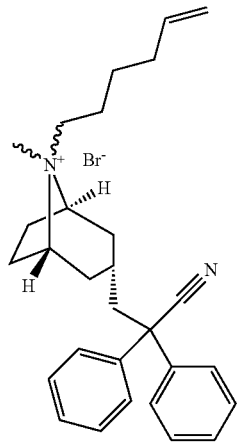

(3-endo)-3-(2-cyano-2,2-diphenylethyl)-8-(5-hexen-1-yl)-8-methyl-8-azoniabicyclo[3.2.1]octane bromide The title compound was prepared in 29% yield by following the general experimental procedure (reaction time=70 hours): LCMS (ES) m/z 413 (M)$^+$; $^1$H-NMR (CDCl$_3$) δ 1.48 (m, 2H), 1.79 (m, 4H), 2.18 (m, 3H), 2.42 (m, 6H), 3.00 (m, 5H), 3.22 (m, 2H), 3.82 (s, 2H), 5.05 (m, 2H), 5.86 (m, 1H), 7.35 (m, 2H), 7.42 (m, 4H), 7.49 (m, 4H).

Example 12

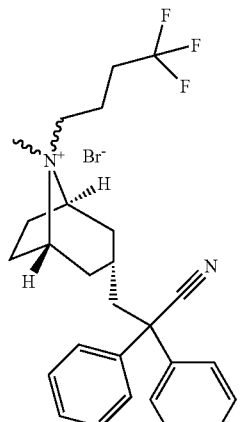

(3-endo)-3-(2-cyano-2,2-diphenylethyl)-8-methyl-8-(4,4,4-trifluorobutyl)-8-azoniabicyclo[3.2.1]octane bromide The title compound was prepared in 23% yield by following the general experimental procedure (reaction time=70 hours): LCMS (ES) m/z 441 (M)$^+$; $^1$H-NMR (CDCl$_3$) δ 1.80

(d, 2H), 2.03 (m, 2H), 2.19 (m, 1H), 2.41 (m, 8H), 3.01 (m, 2H), 3.06 (s, 3H), 3.30 (m, 2H), 3.87 (s, 2H), 7.35 (m, 2H), 7.42 (m, 4H), 7.49 (m, 4H).

Example 13

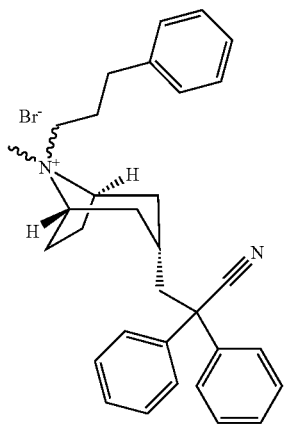

(3-endo)-3-(2-cyano-2,2-diphenylethyl)-8-methyl-8-(3-phenylpropyl)-8-azoniabicyclo[3.2.1]octane bromide The title compound was prepared in 43% yield by following the general experimental procedure (reaction time=7 days): LCMS (ES) m/z 449 (M)+; 1H-NMR (CDCl3) δ 1.78 (d, 2H), 2.07 (m, 2H), 2.26 (m, 4H), 2.46 (m, 3H), 2.71 (t, 2H), 2.97 (d, 2H), 2.99 (s, 3H), 3.21 (m, 2H), 3.80 (s, 2H), 7.25 (m, 2H), 7.31 (m, 4H), 7.41 (m, 5H), 7.47 (m, 4H).

Example 14

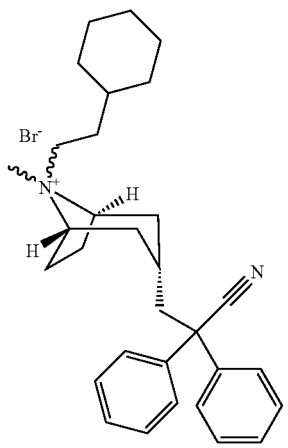

(3-endo)-3-(2-cyano-2,2-diphenylethyl)-8-(2-cyclohexylethyl)-8-methyl-8-azoniabicyclo[3.2.1]octane bromide The title compound was prepared in 21% yield by following the general experimental procedure (reaction time=7 days): LCMS (ES) m/z 441 (M)+; 1H-NMR (CDCl3) δ 1.04 (m, 2H), 1.29 (m, 4H), 1.62 (m, 2H), 1.75 (m, 7H), 2.18 (m, 1H), 2.34 (m, 4H), 2.49 (m, 2H), 3.00 (m, 5H), 3.24 (m, 2H), 3.82 (s, 2H), 7.35 (m, 2H), 7.42 (m, 4H), 7.49 (m, 4H).

Example 15

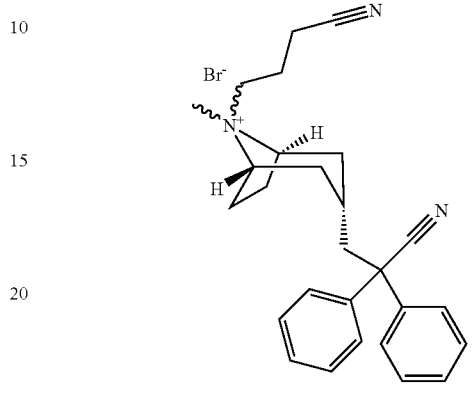

(3-endo)-3-(2-cyano-2,2-diphenylethyl)-8-(3-cyanopropyl)-8-methyl-8-azoniabicyclo[3.2.1]octane bromide The title compound was prepared in 48% yield by following the general experimental procedure (reaction time=7 days): LCMS (ES) m/z 398 (M)+; 1H-NMR (CDCl3) δ 1.83 (d, 2H), 2.17 (m, 3H), 2.42 (m, 6H), 2.60 (t, 2H), 3.01 (m, 2H), 3.06 (s, 3H), 3.32 (m, 2H), 3.87 (s, 2H), 7.35 (m, 2H), 7.42 (m, 4H), 7.49 (m, 4H).

Example 16

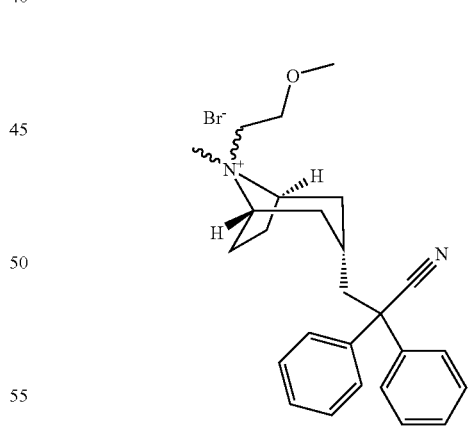

(3-endo)-3-(2-cyano-2,2-diphenylethyl)-8-methyl-8-[2-(methyloxy)ethyl]-8-azoniabicyclo[3.2.1]octane bromide The title compound was prepared in 24% yield by following the general experimental procedure (reaction time=7 days): LCMS (ES) m/z 389 (M)+; 1H-NMR (CDCl3) δ 1.80 (d, 2H), 2.18 (m, 1H), 2.34 (m, 2H), 2.48 (m, 4H), 3.00 (m, 2H), 3.10 (s, 3H), 3.38 (s, 3H), 3.50 (m, 2H), 3.81 (m, 2H), 3.93 (s, 2H), 7.35 (m, 2H), 7.42 (m, 4H), 7.49 (m, 4H).

Example 17

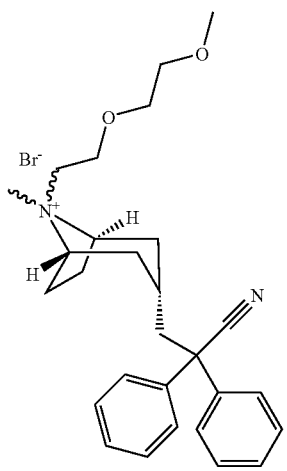

(3-endo)-3-(2-cyano-2,2-diphenylethyl)-8-methyl-8-(2-{[2-(methyloxy)ethyl]oxy}ethyl)-8-azoniabicyclo[3.2.1]octane bromide The title compound was prepared in 28% yield by following the general experimental procedure (reaction time=7 days): LCMS (ES) m/z 433 (M)+; ¹H-NMR (CDCl₃) δ 1.80 (d, 2H), 2.18 (m, 1H), 2.34 (m, 2H), 2.48 (m, 4H), 3.01 (m, 2H), 3.11 (s, 3H), 3.36 (s, 3H), 3.50 (m, 2H), 3.56 (m, 2H), 3.64 (m, 2H), 3.91 (m, 2H), 3.96 (s, 2H), 7.35 (m, 2H), 7.43 (m, 4H), 7.49 (m, 4H).

Intermediate 2

(3-Endo)-tert-butyl 3-(hydroxymethyl)-8-azabicyclo[3.2.1]octane-8-carboxylate

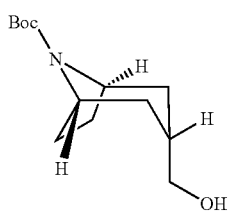

A solution of (3-endo)-(8-benzyl-8-azabicyclo[3.2.1]oct-3-yl)methanol (2.31 g, 10 mmol) in ethanol (45 ml) and 6N HCl (2 ml) containing palladium hydroxide on carbon (Pearlman's catalyst, 2.6 g, 20% (w/w)) was hydrogenated (55 psi H₂) at room temperature for 18 h. After filtration of the catalyst, the filtrate was concentrated under vacuum. The residue was redissolved in EtOH (45 ml) and 6N HCl (2 ml), to which palladium hydroxide on carbon (2.6 g) was added. The reaction mixture was hydrogenated (55 psi H₂) at room temperature for 2 days. The catalyst was filtered off over Celite and the filtrate was evaporated. The residue and di-tert-butyl dicarbonate (3.2 g, 15 mmol) were dissolved in 60 ml of dioxane: 1 N NaOH (2:1) and stirred overnight at room temperature. The solvent was evaporated and the residue partitioned between ethyl acetate (3×50 ml) and water (50 ml). The combined organic layers were dried over Na₂SO₄ and evaporated. The residual oil was purified by loading onto an aminopropyl SPE cartridge (30 g) and eluting with DCM (4×30 ml), EA (4×30 ml) and MeOH (2×30 ml). The DCM fractions were combined and evaporated to give a colourless oil (1.95 g, 81%). LC/MS: 1.65 min (100%), MH+: 242. NMR (CDCl₃): 4.15 ppm (broad, 2H), 3.64 ppm (d, 2H), 2.20 ppm (broad, 2H), 1.97 ppm (broad, 2H), 1.85 ppm (m, 1H), 1.60 ppm (m, 2H), 1.40-1.50 ppm (s+broad, 11H)

Intermediate 3

(3-Endo)-tert-butyl 3-({[(4-methylphenyl)sulfonyl]oxy}methyl)-8-azabicyclo[3.2.1]octane-8-carboxylate

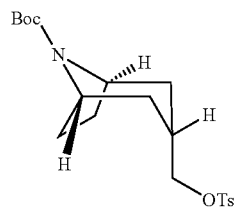

To a solution of (3-endo)-tert-butyl 3-(hydroxymethyl)-8-azabicyclo[3.2.1]octane-8-carboxylate (840 mg, 3.48 mmol) in CH₂Cl₂ (5 ml) was added tosyl chloride (1.33 g, 6.97 mmol) and triethylamine (91 ml, 7.35 mmol). The reaction mixture was stirred at room temperature for 16 hours. The mixture was diluted with 10 ml of DCM and 2 ml of saturated NaHCO₃. The organic layer was isolated with a hydrophobic frit and concentrated under vacuum. The residue was purified by CombiFlash (110 g of Silica, eluting with EA/hexane from 20% to 60% in 65 min.) to afford the title compound (1.24 g, 90%). LC/MS: m/z, 396 (M+H)+, 2.43 min.

Intermediate 4

(3-Endo)-3-(iodomethyl)-8-(phenylmethyl)-8-azabicyclo[3.2.1]octane

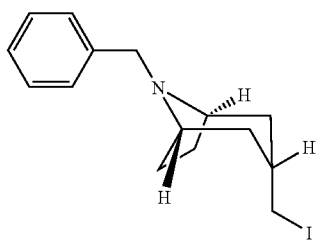

To a solution of iodine (5.08 g, 20 mmol) in DCM (100 ml) was added [8-(phenylmethyl)-8-azabicyclo[3.2.1]oct-3-yl]methanol (2.31 g, 10 mmol) and a polymer supported PPh₃ (9.0 g, 2.21 mmol/g, 20 mmol). After stirring for 17 hours, the reaction mixture was filtered and concentrated under vacuum to afford the title compound (3.07 g, 90%); LC/MS: m/z, 342 (M+H)+, 1.42 min.

Intermediate 5

(3-Endo)-2,2-diphenyl-3-[8-(phenylmethyl)-8-azabicyclo[3.2.1]oct-3-yl]propanenitrile

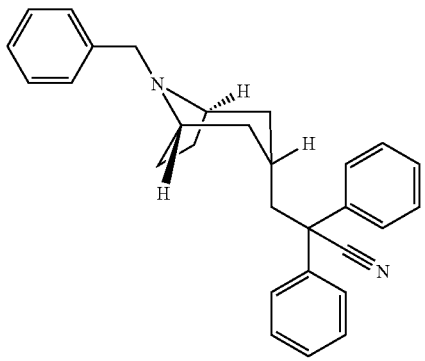

A mixture of (3-endo)-3-(iodomethyl)-8-(phenylmethyl)-8-azabicyclo[3.2.1]octane (2.1 g, 6.16 mmol), Ph$_2$CHCN (3.56 g, 18.5 mmol) and NaH (0.44 g, 18.5 mmol) in a 100 ml round bottom flask was flushed with Argon for 30 min before slowly adding DMF (20 ml) under agitation. The resulting mixture was stirred at room temperature for 60 minutes then diluted with EA (200 ml) and water (100 ml). The aqueous layer was separated and extracted with EA (2×100 ml). The combined organic layers were evaporated, and the residue was purified by CombiFlash (110 g of Silica, eluting with EA/hexane from 20% to 60% in 65 min.) to afford the title compound (1.50 g, 60%); LC/MS: m/z, 407 (M+H)+, 1.90 min; 1H-NMR (CDCl$_3$) 1.29 (d, 2H), 1.74 (m, 2H), 2.04-2.15 (m, 5H), 2.66 (s, 2H), 3.15 (s, 2H), 3.52 (s, 2H), 7.24-7.41 (m, 15H).

Intermediate 6

(3-Endo)-3-(8-azabicyclo[3.2.1]oct-3-yl)-2,2-diphenylpropanenitrile

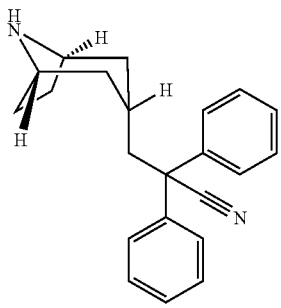

a) From (3-Endo)-2,2-diphenyl-3-[8-(phenylmethyl)-8-azabicyclo[3.2.1]oct-3-yl]propanenitrile To a solution of (3-endo)-2,2-diphenyl-3-[8-(phenylmethyl)-8-azabicyclo[3.2.1]oct-3-yl]propanenitrile (82 mg, 0.2 mmol) in 1.5 ml of DCE at 0° C., was slowly added 1-chloroethyl chloroformate (115 mg, 0.8 mmol). The mixture was heated in a microwave at 140° C. for 80 min. LC/MS showed ~70% of the desired product and 13% of the starting material. Further extension of the reaction time didn't improve the yield as assessed by LC/MS. The reaction mixture was quenched with 1 ml of MeOH and allowed to heat at reflux for 1 h. After evaporation of the solvent, the residue was purified by reverse-phase Gilson HPLC, eluting with eluting with acetonitrile/water/0.1% TFA (10/90 to 70/30, v/v, over 12 min), to give the title compound (56 mg, 88%). LC/MS: m/z, 317 (M+H), 1.54 min.

b) From (3-endo)-tert-butyl 3-({[(4-methylphenyl)sulfonyl]oxy}methyl)-8-azabicyclo[3.2.1]octane-8-carboxylate To a mixture of (3-endo)-tert-butyl 3-({[(4-methylphenyl)sulfonyl]oxy}methyl)-8-azabicyclo[3.2.1]octane-8-carboxylate (0.46 g, 1.16 mmol), Ph$_2$CHCN (0.67 g, 3.31 mmol) and NaH (84 mg, 3.5 mmol) was slowly added 6 ml of dry DMF under Argon for 10 min. The resulting mixture was heated in a microwave reactor at 220° C. for 60 minutes. The solution was filtered and purified by Gilson reverse-phase HPLC eluting with acetonitrile/water/0.1% TFA (10/90 to 70/30, v/v, over 12 min), to give the title compound as a TFA salt (400 mg, 80%). LC/MS: m/z, 317 (M+H), 1.64 min.

Intermediate 7

(3-Endo)-3-[8-(5-hexen-1-yl)-8-azabicyclo[3.2.1]oct-3-yl]-2,2-diphenylpropanenitrile

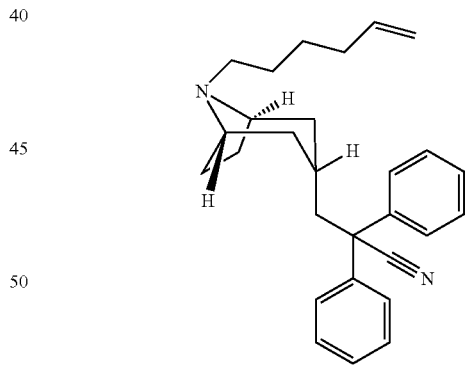

To a solution of (3-endo)-3-(8-azabicyclo[3.2.1]oct-3-yl)-2,2-diphenylpropanenitrile (TFA salt, 256 mg, 0.59 mmol) in 10 ml of dry acetonitrile, was added 6-bromo-1-hexene (108 mg, 0.65 mmol) and K$_2$CO$_3$ (447 mg, 3.24 mmol). The mixture was heated at reflux for 16 hours, filtered and concentrated under vacuum. The crude residue was purified by loading onto a 10 g aminopropyl SPE cartridge, eluting sequentially with toluene (3×5 ml) and EA (3×5 ml). The toluene fractions 2 and 3 and the EA fractions 1 and 2 were combined and evaporated to give the title compound as pale yellow oil (150 mg, 64%). LC/MS: m/z, 399 (M+H), 1.93 min.

Example 18

N-(Endo)-(3-endo)-3-(2-cyano-2,2-diphenylethyl)-(8-endo)-8-(5-hexen-1-yl)-8-methyl-8-azoniabicyclo[3.2.1]octane bromide

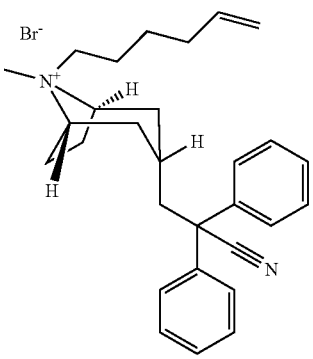

To a solution of (3-endo)-3-[8-(5-hexen-1-yl)-8-azabicyclo[3.2.1]oct-3-yl]-2,2-diphenylpropanenitrile (300 mg, 0.75 mmol) in 1 ml of acetone, was added bromomethane in t-butyl ether (2 M, 7.5 ml, 15 mmol) and $K_2CO_3$ (104 mg, 0.75 mmol) followed by stirring at room temperature for 16 hours. After addition of DCM (20 ml) and filtration, the filtrate was concentrated under vacuum to give a crude product, which was recrystallized with DCM/EA/hexane to give ~250 mg of a white solid, containing ~5% exo isomer as assessed by NMR. Another recrystallization under the same conditions gave the pure endo isomer (148 mg, 40%). LC/MS: m/z, 413 (M+H), 1.93 min.

Intermediate 8

(3-Endo)-2,2-diphenyl-3-(8-{(2-[(phenylmethyl)oxy]ethyl}-8-azabicyclo[3.2.1]oct-3-yl)propanenitrile

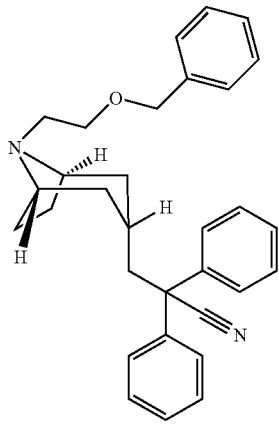

Following the standard procedure outlined for Intermediate 7, (3-endo)-3-(8-azabicyclo[3.2.1]oct-3-yl)-2,2-diphenylpropanenitrile (TFA salt, 160 mg, 0.37 mmol) was reacted with 2-bromoethyl phenylmethyl ether (80 mg, 0.37 mmol) to give the title compound (150 mg, 90%). LC/MS: m/z, 451 (M+H), 1.93 min.

Intermediate 9

(3-Endo)-2,2-diphenyl-3-[8-(3-phenylpropyl)-8-azabicyclo[3.2.1]oct-3-yl]propanenitrile

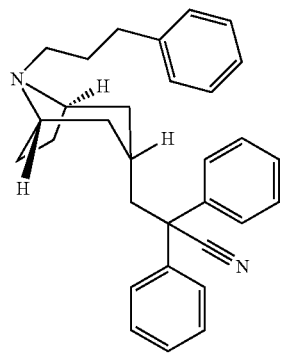

Following the standard procedure outlined for Intermediate 7, (3-endo)-3-(8-azabicyclo[3.2.1]oct-3-yl)-2,2-diphenylpropanenitrile (TFA salt, 160 mg, 0.37 mmol) was reacted with 3-bromopropylbenzene (74 mg, 0.37 mmol) to give the title compound (140 mg, 87%). LC/MS: m/z, 435 (M+H), 1.85 min.

Intermediate 10

(3-Endo)-2,2-diphenyl-3-{8-[3-(phenyloxy)propyl]-8-azabicyclo[3.2.1]oct-3-yl}propanenitrile

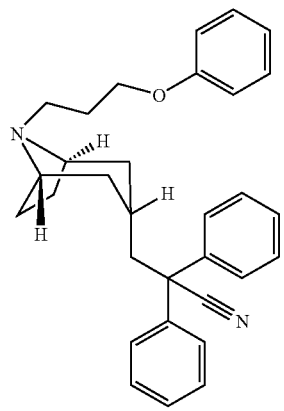

Following the standard procedure outlined for Intermediate 7, (3-endo)-3-(8-azabicyclo[3.2.1]oct-3-yl)-2,2-diphenylpropanenitrile (TFA salt, 160 mg, 0.37 mmol) was reacted with 3-bromopropyl phenyl ether (80 mg, 0.37 mmol) to give the title compound (150 mg, 90%). LC/MS: m/z, 451 (M+H), 2.00 min.

Example 19

N-(Endo)-(3-endo)-(2-cyano-2,2-diphenylethyl)-(8-endo)methyl-8-{2-[(phenylmethyl)oxy]ethyl}-8-azoniabicyclo[3.2.1]octane bromide

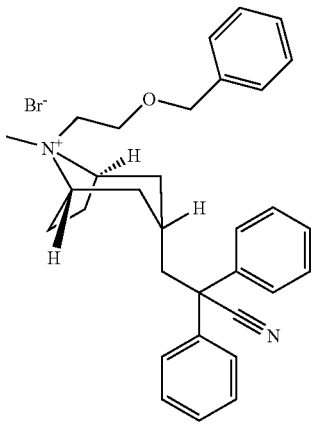

Following the standard procedure outlined in Example 18, (3-endo)-2,2-diphenyl-3-(8-{2-[(phenylmethyl)oxy]ethyl}-8-azabicyclo[3.2.1]oct-3-yl)propanenitrile (150 mg, 0.33 mmol) was reacted with bromomethane (2M, 3.3 ml, 6.6 mmol) to give the title compound (115 mg, 63%). LC/MS: m/z, 465 (M+H), 2.01 min.

Example 20

N-(Endo)-(3-endo)-(2-cyano-2,2-diphenylethyl)-8-methyl-8-(3-phenylpropyl)-8-azoniabicyclo[3.2.1]octane bromide

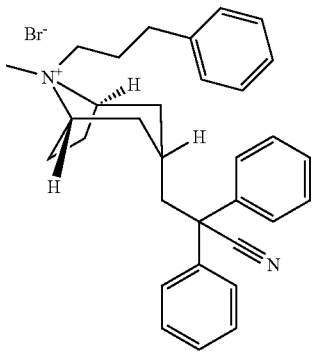

Following the standard procedure outlined in Example 18, (3-Endo)-2,2-diphenyl-3-[8-(3-phenylpropyl)-8-azabicyclo[3.2.1]oct-3-yl]propanenitrile (140 mg, 0.3 mmol) was reacted with bromomethane (2M, 3.2 ml, 6.4 mmol) to give the title compound (100 mg, 59%). LC/MS: m/z, 449 (M+H), 2.02 min.

Example 21

N-(Endo)-(3-endo)-(2-cyano-2,2-diphenylethyl)-8-methyl-8-[3-(phenyloxy)propyl]-8-azoniabicyclo[3.2.1]octane bromide

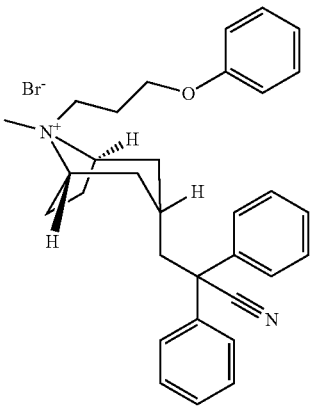

Following the standard procedure outlined Example 18, (3-endo)-3-(8-azabicyclo[3.2.1]oct-3-yl)-2,2-diphenylpropanenitrile (150 mg, 0.33 mmol) was reacted with bromomethane (2M, 3.3 ml, 6.6 mmol) to give the title compound (115 mg, 63%). LC/MS: m/z, 465 (M+H), 2.04 min.

| Abbreviations | |
|---|---|
| BOC | tert-butyloxycarbonyl |
| DCM | Dichloromethane |
| DMF | Dimethylformamide |
| DMSO | Dimethylsulfoxide |
| ES | Electrospray ionization |
| HPLC | High pressure liquid chromatography |
| LCMS | Liquid chromatography mass spectrometry |
| NMR | Nuclear magnetic resonance |
| SPE | Solid phase extraction |
| TEA | Triethylamine |
| TFA | Trifluoroacetic acid |
| THF | Tetrahydrofuran |
| TLC | Thin layer chromatography |

BIOLOGICAL EXAMPLES

The inhibitory effects of compounds at the $M_3$ mAChR of the present invention are determined by the following in vitro and in vivo assay:

Analysis of Inhibition of Receptor Activation by Calcium Mobilization:

Stimulation of mAChRs expressed on CHO cells were analyzed by monitoring receptor-activated calcium mobilization as previously described[10]. CHO cells stably expressing $M_3$ mAChRs were plated in 96 well black wall/clear bottom plates. After 18 to 24 hours, media was aspirated and replaced with 100 µl of load media (EMEM with Earl's salts, 0.1% RIA-grade BSA (Sigma, St. Louis Mo.), and 4 µM Fluo-3-acetoxymethyl ester fluorescent indicator dye (Fluo-3 µM, Molecular Probes, Eugene, Oreg.) and incubated 1 hr at 37° C. The dye-containing media was then aspirated, replaced with fresh media (without Fluo-3 µM), and cells were incubated for 10 minutes at 37° C. Cells were then washed 3 times and incubated for 10 minutes at 37° C. in 100 µl of assay buffer (0.1% gelatin (Sigma), 120 mM NaCl, 4.6 mM KCl, 1 mM $KH_2PO_4$, 25 mM $NaHCO_3$, 1.0 mM $CaCl_2$, 1.1 mM $MgCl_2$, 11 mM glucose, 20 mM HEPES (pH 7.4)). 50 µl of compound ($1\times10^{-11}$-$1\times10^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 µl of acetylcholine (0.1-10 nM final), prepared in buffer containing 0.1% BSA, at a rate of 50 µl/sec. Calcium mobilization, monitored as change in cytosolic calcium concentration, was measured as change in 566 nm emission intensity. The change in emission intensity is directly related to cytosolic calcium levels[11]. The emitted fluorescence from all 96 wells is measured simultaneously using a cooled CCD camera. Data points are collected every second. This data was then plotting and analyzed using GraphPad PRISM software.

Methacholine-induced Bronchoconstriction

Airway responsiveness to methacholine was determined in awake, unrestrained BalbC mice (n=6 each group). Barometric plethysmography was used to measure enhanced pause (Penh), a unitless measure that has been shown to correlate with the changes in airway resistance that occur during bronchial challenge with methacholine[12]. Mice were pretreated with 50 µl of compound (0.003-10 µg/mouse) in 50 µl of vehicle (10% DMSO) intranasally, and were then placed in the plethysmography chamber. Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software.

Muscarinic Receptor Radioligand Binding Assays

Radioligand binding studies using 0.5 nM [$^3$H]-N-methyl scopolamine (NMS) in a SPA format is used to assess binding of muscarinic antagonists to $M_1$, $M_2$, $M_3$, $M_4$ and $M_5$ muscarinic acetylcholine receptors. In a 96-well plate, the SPA beads are pre-incubated with receptor-containing membrane for 30 min at 4° C. Then 50 mM HEPES and the test compound are added and incubated at room temperature (shaking) for 2 hours. The beads are then spun down and counted using a scintillation counter.

Evaluation of Potency and Duration of Action in Isolated Guinea Pig Trachea

Tracheae were removed from adult male Hartely guinea pigs (Charles River, Raleigh, N.C.; 400-600 grams) and placed into modified Krebs-Henseleit solution. Composition of the solution was (mM): NaCl 113.0, KCl 4.8, $CaCl_2$ 2.5, $KH_2PO_4$ 1.2, $MgSO_4$ 1.2, $NaHCO_3$ 25.0 and dextrose 11.0. which was gassed with 95% $O_2$:5% $CO_2$ and maintained at 37° C. Each trachea was cleaned of adherent tissue and opened lengthwise. Epithelium was removed by gently rubbing the luminal surface with a cotton-tipped applicator. Individual strips were cut, approximately 2 cartilage rings in width, and suspended via silk suture in 10-ml water-jacketed organ baths containing Krebs-Henseleit solution and connected to Grass FT03C force-displacement transducers. Mechanical responses were recorded isometrically by MP100WS/Acknowledge data acquisition system (BIOPAC Systems, Goleta, Calif., www.biopac.com) run on Apple G4 computers. The tissues were equilibrated under a resting tension of 1.5 g, determined to be optimal by length-tension evaluation, and washed with Krebs-Henseleit solution every 15 minutes for one hour. After the equilibration period pulmonary tissues were contracted with 10 uM carbachol until reaching plateau, which served as a reference contraction for data analysis. Tissues were then rinsed every 15 minutes over 1 hour until reaching baseline tone. The preparations were then left for at least 30 minutes before the start of the experiment.

Concentration-response curves were obtained by a cumulative addition of carbachol in half-log increments (Van Rossum, 1963, Arch. Int. Pharmacodyn., 143:299), initiated at 1 nM. Each concentration was left in contact with the preparation until the response plateaued before the addition of the subsequent carbachol concentration. Paired tissues were exposed to mAChR antagonist compounds or vehicle for 30 min before carbachol cumulative concentration-response curves were generated. All data is given as mean ±standard error of the mean (s.e.m.) with n being the number of different animals.

For superfusion (duration of action) studies, the tissues were continuously superfused with Krebs-Henseleit solution at 2 ml/min for the duration of the experiment. Stock solutions of agonist and antagonist were infused (0.02 ml/min) via 22-gauge needle inserted into the superfusion tubing. Mechanical responses were recorded isometrically using a commercially-available data acquisition system (MP100WS/Acknowledge; BIOPAC Systems, Goleta, Calif., www.biopac.com) interfaced with a Macintosh G4 computer (Apple, Cupertino, Calif. www.apple.com). The tissues were suspended under an optimal resting tension of 1.5 g. After a 60 min equilibration period, the tissues were contracted with carbachol (1 uM) for the duration of the experiment. Upon reaching a sustained contraction isoproterenol (10 uM) was administered to maximally relax the tissue, and this change served as a reference. Isoproterenol exposure was halted and the carbachol-induced tension allowed to recover. Muscarinic receptor antagonists infused at a single concentration per tissue until a sustained level of inhibition was attained. The compound was then removed and, once again, the carbachol-induced tension was allowed to recover.

The following parameters were determined for each concentration of antagonist, and expressed as the mean ±S.E.M. for n individual animals. Inhibition of the carbachol-induced contraction was expressed as a percent of the reference response (isoproterenol) and the time required to reach one-half of this relaxation was measured (onset of response). The tension recovery following removal of the compound was determined as was the time required to reach one-half of the maximum tension recovery (offset of response). At 60 and 180 minutes after removal of the antagonist the remaining level of inhibition was determined and expressed as a percent of the isoproterenol reference.

Antagonist concentration-response curves were obtained by plotting the maximal relaxation data at 0, 60 and 180-min following antagonist withdrawal. Recovery, termed shift, was calculated from the ratio of the 0-min inhibition curve $IC_{50}$ and the concentration of compound yielding a similar tension recovery at 60 and 180 minutes.

Halftimes for onset and offset of response were plotted vs. corresponding concentration and the data were fit with non-linear regression. These values were extrapolated at the $IC_{50}$ (determined from the inhibition concentration-response curve) and designated $Ot_{50}$ (time required, at the $IC_{50}$ concentration, to reach half of the onset response) and $R_t50$ (time required, at the $IC_{50}$ concentration, to reach half of the recovery response).

Formulation-Administration

Accordingly, the present invention further provides a pharmaceutical formulation comprising a compound of formula (I), or a pharmaceutically acceptable salt, solvate, or physiologically functional derivative (e.g., salts and esters) thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

Compounds of formula (I) will be administered via inhalation via the mouth or nose.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di- or polysaccharides (e.g., lactose or starch), organic or inorganic salts (e.g., calcium chloride, calcium phosphate or sodium chloride), polyalcohols (e.g., mannitol), or mixtures thereof, alternatively with one or more additional materials, such additives included in the blend formulation to improve chemical and/or physical stability or performance of the formulation, as discussed below, or mixtures thereof. Use of lactose is preferred. Each capsule or cartridge may generally contain between 20 μg-10 mg of the compound of formula (I) optionally in combination with another therapeutically active ingredient. Alternatively, the compound of the invention may be presented without excipients, or may be formed into particles comprising the compound, optionally other therapeutically active materials, and excipient materials, such as by co-precipitation or coating.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant as an inhaler having a reservoir form pack suitable for comprising multiple (un-metered doses) of medicament in dry powder form and including means for metering medicament dose from the reservoir to a delivery position. The metering means may for example comprise a metering cup or perforated plate, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (e.g. as in Diskus, see GB 2242134 or Diskhaler, see GB 2178965, 2129691 and 2169265) or metered in use (e.g. as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disk-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants e.g. oleic acid or lecithin and co solvents e.g. ethanol.

Pressurized formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum aerodynamic particle size for inhalation into the bronchial system for localized delivery to the lung is usually 1-10 μm, preferably 2-5 μm. The optimum aerodynamic particle size for inhalation into the alveolar region for achieving systemic delivery to the lung is approximately 0.5-3 μm, preferably 1-3 μm. Particles having an aerodynamic size above 20 μm are generally too large when inhaled to reach the small airways. Average aerodynamic particle size of a formulation may measure by, for example cascade impaction. Average geometric particle size may be measured, for example by laser diffraction, optical means.

To achieve a desired particle size, the particles of the active ingredient as produced may be size reduced by conventional means e.g. by controlled crystallization, micronization or nanomilling. The desired fraction may be separated out by air classification. Alternatively, particles of the desired size may be directly produced, for example by spray drying, controlling the spray drying parameters to generate particles of the desired size range. Preferably, the particles will be crystalline, although amorphous material may also be employed where desirable. When an excipient such as lactose is employed, generally, the particle size of the excipient will be much greater than the inhaled medicament within the present invention, such that the "coarse" carrier is non-respirable. When the excipient is lactose it will typically be present as milled lactose, wherein not more than 85% of lactose particles will have a MMD of 60-90 μm and not less than 15% will have a MMD of less than 15 μm. Additive materials in a dry powder blend in addition to the carrier may be either respirable, i.e., aerodynamically less than 10 microns, or non-respirable, i.e., aerodynamically greater than 10 microns.

Suitable additive materials which may be employed include amino acids, such as leucine; water soluble or water insoluble, natural or synthetic surfactants, such as lecithin (e.g., soya lecithin) and solid state fatty acids (e.g., lauric, palmitic, and stearic acids) and derivatives thereof (such as salts and esters); phosphatidylcholines; sugar esters. Additive materials may also include colorants, taste masking agents (e.g., saccharine), antistatic-agents, lubricants (see, for example, Published PCT Patent Appl. No. WO 87/905213, the teachings of which are incorporated by reference herein), chemical stabilizers, buffers, preservatives, absorption enhancers, and other materials known to those of ordinary skill.

Sustained release coating materials (e.g., stearic acid or polymers, e.g. polyvinyl pyrolidone, polylactic acid) may also be employed on active material or active material containing particles (see, for example, U.S. Pat. No. 3,634,582, GB 1,230,087, GB 1,381,872, the teachings of which are incorporated by reference herein).

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as herein before recited, or an appropriate fraction thereof, of the active ingredient.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I)

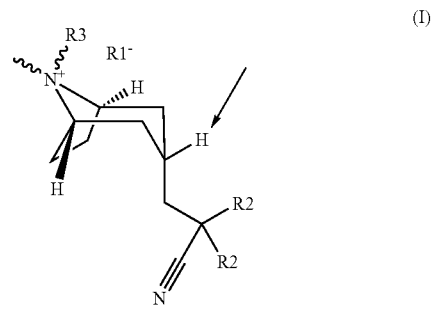

wherein:
R1⁻ represents a pharmaceutically acceptable anion associated with the positive charge of the N atom;
R2 is aryl;
R3 is (C₁-C₆)alkyl-O—(C₁-C₆alkyl) aryl; and wherein the H atom indicated is in the exo position.

2. The compound according to claim 1 wherein R1⁻ is selected from the group consisting of chloride, bromide, iodide, sulfate, benzene sulfonate and toluene sulfonate.

3. The compound according to claim 1 wherein R2 is phenyl.

4. The compound according to claim 1 wherein
R3 is —(C₂ alkyl)—O—(C₁alkyl)-aryl.

5. The compound according to claim 4 wherein the aryl in R3 is a phenyl.

6. The compound according to claim 1 wherein the aryl in R3 is a phenyl.

7. The compound according to claim 6 wherein R2 is phenyl.

8. The compound according claim 1 which is
N-(Endo)-(3-endo)-(2-cyano-2,2-diphenylethyl)-(8-endo)-methyl-8-{2-[(phenylmethyl)oxy]ethyl}-8-azoniabicyclo[3.2.1]octane bromide.

9. A pharmaceutical composition comprising a compound according to claim 1 and a pharmaceutically acceptable carrier thereof.

10. A pharmaceutical composition comprising a compound according to claim 8 and a pharmaceutically acceptable carrier thereof.

11. The compound according to claim 7 wherein
$R1^-$ is selected from the group consisting of chloride, bromide, iodide, sulfate, benzene sulfonate and toluene sulfonate.

12. The compound N-(Endo)-(3-endo)-(2-cyano-2,2-diphenylethyl)-(8-endo)-methyl-8-{2-[(phenylmethyl)oxy]ethyl}-8-azoniabicyclo[3.2.1]octane and a pharmaceutically acceptable anion thereof.

13. A pharmaceutical composition comprising a compound according to claim 12 and a pharmaceutically acceptable carrier or diluent.

14. The compound according to claim 12 wherein the pharmaceutically acceptable anion is chloride, bromide, iodide, sulfate, benzene sulfonate or toluene sulfonate.

15. The compound according to claim 14 wherein the anion is chloride.

16. The compound according to claim 14 wherein the anion is bromide.

17. The compound according to claim 14 wherein the anion is iodide.

18. The compound according to claim 14 wherein the anion is sulfate.

19. The compound according to claim 14 wherein the anion is benzene sulfonate.

20. The compound according to claim 14 wherein the anion is toluene sulfonate.

21. A pharmaceutical composition comprising a compound according to claim 14 and a pharmaceutically acceptable carrier or diluent.

22. The compound according to claim 5 wherein R2 is phenyl.

23. The compound according to claim 22 wherein $R1^-$ is selected from the group consisting of chloride, bromide, iodide, sulfate, benzene sulfonate and toluene sulfonate.

* * * * *